United States Patent [19]

Cassel et al.

[11] Patent Number: 4,990,701

[45] Date of Patent: Feb. 5, 1991

[54] HALOGEN EXCHANGE FLUORINATION

[75] Inventors: Wendel R. Cassel, Newark; Richard E. Fernandez, Bear, both of Del.; Frederick W. Mader, Kennett Square, Pa.

[73] Assignee: E. I. DuPont de Nemours and Company, Wilmington, Del.

[21] Appl. No.: 497,067

[22] Filed: Mar. 20, 1990

[51] Int. Cl.$^5$ ............................................. C07C 17/20
[52] U.S. Cl. .................................................. 570/170
[58] Field of Search ....................................... 570/170

[56] References Cited

U.S. PATENT DOCUMENTS 4,311,863  1/1982  Gumprecht .................. 570/170

FOREIGN PATENT DOCUMENTS 941144  11/1963  United Kingdom .

Primary Examiner—Alan Siegel

[57] ABSTRACT

A process for halogen exchange fluorination by contacting a halocarbon having a replaceable halogen other than fluorine with KF.nHF wherein n is 0.5–3 to provide a fluorinated hydrocarbon having at least one more fluorine than the starting halocarbon and, optionally, regenerating the KF.nHF with additional HF, or in a continuous process, with excess HF in the feed.

11 Claims, No Drawings

HALOGEN EXCHANGE FLUORINATION

FIELD OF INVENTION

This invention relates to the halogen exchange fluorination of saturated halocarbons to the corresponding halocarbon having at least one additional fluorine-substitution than the original halocarbon. More particularly, the invention relates to the conversion of a saturated halocarbon having at least one chlorine or bromine substitution to the corresponding halocarbon having at least one fluorine substitution replacing the "at least one chlorine or bromine substitution." Of greatest interest is the invented process for improving the conversion of 2-chloro- or 2-bromo-1,1,1-trifluorethane, $CF_3CH_2Cl$ or $CF_3CH_2Br$, hereinafter referred to as "HCFC-133a" and "HBFC-133aBl" respectively, to 1,1,1,2-tetra-fluoroethane, $CF_3CH_2F$, hereinafter referred to as "HFC-134a" and, optionally, recovering the resulting metal chloride or bromide as the metal fluoride for recycling into the conversion process.

BACKGROUND OF THE INVENTION

HFC-134a and its isomer, 1,1,2,2-tetrafluoroethane, $CHF_2$-$CHF_2$, hereinafter referred to as "HFC-134", are potentially useful as aerosol propellants and as refrigerants. They are of particular interest as replacements for Freon ® 12, the commercial refrigerant currently used in substantially all automotive air conditioning systems.

Heretofore, however, the production of HFC-134 and HFC-134a has not been commercially attractive. In particular, a definite need exists for converting HCFC-133a to HFC-134a by a process that is readily adaptable to continuous operation, that minimizes the need for hydrogen fluoride as a fluorine source, that provides the desired tetrafluoro compound at high conversion and selectivity levels and that provides the desired compound in a high state of purity.

PRIOR ART

As stated in U.S. Pat. No. 4,311,863, (column 1, lines 26 ff.) "It is apparent from the prior art that the chlorine atom of the —$CH_2Cl$ group (as in HCFC-133a) is highly resistant to halogen exchange with HF." As "prior art," the inventor in this patent discloses the following references: U.S. Pat. No. 2,885,427; U.S. Pat. No. 3,664,545; U.S. Pat. No. 4,129,603; and in a book by Hudlicky p. 93 of "Chemistry of Organic Fluorine Compounds", MacMillan Co., New York, N.Y. (1962).

U.S. Pat. No. 2,885,427 discloses the preparation of HFC-134a by the vapor phase reaction of trichloroethylene with HF in the presence of a catalyst prepared by heating hydrated chromium fluoride in the presence of oxygen. The resultant product is a mixture of fluorocarbons in which HFC-134a is reported as being present in an amount of 3 mol %.

Hudlicky in his book and U.S. Pat. No. 3,644,545 disclose the difficulty of fluorine exchange on —$CH_2Cl$ groups with HF in an antimony-catalyzed liquid phase reaction and in a vapor phase reaction, respectively.

U.S. Pat. No. 4,129,603 discloses the vapor phase reaction of CFC-133a with HF in the presence of chromium oxide catalyst to produce a fluorocarbon mixture in which the HFC-134a is reported as 18.2% by volume.

U.S. Pat. No. 1,914,135; Australian Patent No. 3,141; U.S. Pat. No. 2,739,989; and U.S. Pat. No. 3,843,546 disclose halogen exchange fluorination using alkali metal or alkaline earth metal fluorides. However, these metal fluorides have relatively low orders of reactivity; and processes involving them are generally best conducted in the vapor phase at elevated temperature of 350° to 550° C. by passing the gaseous halocarbon over or through a bed of the solid metal fluoride. The metal halide by-product tends to coat the metal fluoride as reaction progresses so that the reaction rate is retarded; frequent changes of metal fluoride are necessitated; and other expedients, as set forth in these patents, must be imposed to ameliorate the problem.

British Patent No. 941,144 discloses that the elevated temperatures required in the gas-solid processes can be reduced and the yields improved by employing a gas-liquid process. A gaseous chlorocarbon is passed through a metal fluoride-metal chloride melt at a temperature of about 300° to 375° C. The metal fluorides disclosed are, inter alia, sodium, potassium and calcium fluorides. The molten metal chloride which functions as a solvent for the fluoride may be ferric or zinc chloride or mixtures thereof or these mixtures with sodium chloride.

U.S. Pat. No. 4,311,863 discloses a gas-liquid halogen exchange process in an aqueous medium. Specifically, the process involves converting HCFC-133a to HFC-134a by reaction with potassium, cesium or rubidium fluoride in a 25 to 65 weight % aqueous solution at about 200° to 300° C. under autogenous pressure. Although the process can provide adequate yields of HFC-134a, it is not readily adaptable to low cost, economic, continuous operation, particularly in view of the higher pressures required to maintain the aqueous mixture in the liquid state at the operating temperatures required and the excessive corrosion of the reactor materials under process conditions. It should be noted that at column 5, line 34 ff. of this patent, it is disclosed that "HF in the absence of water does not further the reaction. . . . 2-chloro-1,1,1-trifluoroethane (CFC-133a) was contacted with fused KF.HF with no water present. No reaction occurred." (Underlines added).

SUMMARY OF INVENTION

The present invention is a process for the halogen exchange fluorination of a saturated halocarbon, preferably a continuous process, comprising the following steps:

1. Intimately contacting a halocarbon having at least one replaceable halogen other than fluorine, i.e., chlorine or bromine, in the molecule with an anhydrous molten composition containing at least 50 mole % of a compound having the formula KF.nHF wherein "n" is a number from about 0.5 to 3, preferably about 0.5 to 1, at a temperature of about 30° C. to just below the lower of the decomposition temperature of the original halocarbon or that of the fluorinated product, preferably about 200° C. to about 350° C., at a subatmospheric or superatmospheric pressure as high as 2000 psi, preferably the latter for increased productivity, usually 14.7 psi to about 1500 psi, for a period of a few seconds to several hours, usually 0.5 minute to two hours, i.e., a pressure and time sufficient to provide at least one reaction product having at least one more fluorine atom in the molecule than the original halocarbon and a residual molten composition at least partially depleted in fluoride content and enriched in its other-than-fluoride halide content;

2. Isolating and recovering the fluorinated reaction product from the residual molten composition; and, optionally,
3. Contacting the residual composition with anhydrous HF in the presence or absence of the halocarbon to convert the other-than-fluoride halide content to HX wherein X is chlorine or bromine, and separating the gaseous HX from the molten composition.

The process of this invention, particularly when HCFC-133a is the saturated halocarbon, is to intimately contact HCFC-133a with molten KF.HF at a temperature of 180° C. to 350° C. to produce HFC-134a in high conversions, high yields and in a high state of purity without any substantial amount of objectionable unsaturated by-products. Optionally, the potassium chloride produced in the conversion may be treated with additional HF to regenerate potassium fluoride accompanied by the production of gaseous HCl which is removed from the operation. The potassium fluoride is recycled with HF to form KF.nHF, which in turn serves to convert additional HCFC-133a to HFC-134a.

In the preferred continuous process, the fluorinatable saturated halohydrocarbon is cofed with HF into a continuous feed stirred tank reactor, known in the art as a "CFSTR", the amount of HF being sufficient to carry out the fluorination of the saturated halocarbon and the regeneration of the KF.nHF from the potassium halide formed during fluorination continuously and simultaneously.

Specifically where HCFC-133a is the saturated halocarbon and KF.HF is used, HCFC-133a is cofed with HF into a CFSTR containing the molten composition containing at least 50 mole % of KF.HF at a temperature of 180° C. to 350° C. to produce HFC-134a and, with the excess HF, simultaneously convert KCl (Formed along with HFC-134a as shown in equation (2) below) to KF with the continuous release of HCl. The HFC-134a is isolated and further purified, if necessary, before being stored for ultimate sale as a refrigerant or otherwise.

The following equations depict the theory of operation of this invention:

$$KF.nHF \rightarrow KF + nHF \quad (1)$$

$$KF + 133a \rightarrow 134a + KCl \quad (2)$$

$$KCl + nHF \rightarrow HCl + KF.nHF \quad (3)$$

Equation (1) represents the first step of the process in which the molten composition is formed. Equation (2) represents the halogen exchange stage in which the HCFC-133a is passed through the molten composition to yield HFC-134a, which is removed as a gas and recovered as a liquid. Equation (3) represents the regeneration stage in which the KF is reformed from KCl and combined with additional HF to form the molten composition of KF.nHF.

The invention is applicable to the fluorination of saturated halocarbons having one or more replaceable halogens other than fluorine. The term "saturated" used herein is meant to include halocarbons wherein the halogen to be replaced by fluorine is bonded to a saturated, that is, sp3 hybridized carbon atom that, in turn, is bonded only to hydrogen, halogen, or another sp3 hybridized carbon atom. In other words, any constituent containing carbon-carbon unsaturation, if present, will be at least two carbon atoms removed from the carbon atom bearing the halogen to be replaced.

The saturated halocarbons can be composed of carbon and halogen or of carbon, hydrogen and halogen, where halogen stands for fluorine, chlorine, bromine, or iodine, with at least one of the halogen atoms being other than fluorine. Preferably, the halogen atoms other-than-fluorine will be chlorine or bromine; more preferably, chlorine because of the greater availability and broader utility of compounds containing chlorine. Included are perhalocarbons, composed of carbon and halogen, and halohydrocarbons composed of carbon, hydrogen, and halogen. The hydrogen-containing halocarbons are preferred because of the low ozone depletion potentials of their fluorinated derivatives. Overall, the halocarbons will normally contain 1 to 6 carbon atoms, preferably at least 2 carbons, more preferably 2 to 3 carbons, most preferably 2 carbon atoms because of their greater commercial importance. They will have normal boiling points in the range of −80° to 130° C., more usually −40° to 120° C. Included are alicyclic as well as acyclic compounds.

The fluorinated hydrocarbon products that may be prepared by the invented process can comprise carbon and halogen or carbon, hydrogen and halogen, with at least one halogen being a fluorine atom. Included are unsaturated as well as saturated fluorinated hydrocarbons, as illustrated in the accompanying table. Preferred products contain hydrogen in addition to fluorine, with chlorine optionally present.

One of the advantages of the invented process over those disclosed previously lies in the structure of the fluorinated product. It has been found that the structure of the other-than-fluoride halide-containing saturated halocarbon is largely preserved after fluorination in the fluorinated hydrocarbon product without rearrangement to undesirable isomers. In prior art processes, the product tends to rearrange to form the thermodynamically most stable product. Thus, HCFC-133 tends to yield HFC-134a, instead of the desired HFC-134, in the processes of the prior art.

Representative fluorinatable halocarbons and fluorinated hydrocarbons that can be produced therefrom in accordance with the process of the invention are listed in the following table. It should be understood that the compounds listed in the table are not all inclusive; and that one skilled in the art may use the invention to form additional fluorinated hydrocarbons from other fluorinatable hydrocarbons.

| Halocarbon Reactants | | Fluorinated Hydrocarbon Products | |
|---|---|---|---|
| $CHCl_3$ | $CCl_4$ | $CHCl_2F$ | $CCl_2FCH_2Cl$ |
| $CHCl_2F$ | $CCl_3F$ | $CHClF_2$ | $CClF_2CH_2Cl$ |
| $CHClF_2$ | $CCl_2F_2$ | $CHF_3$ | $CF_3CH_2Cl$ |
| $CH_3CH_2Br$ | $CH_3CCl_3$ | $CClF_3$ | $CF_3CH_2F$ |
| $CH_2ClCH_2Cl$ | $CH_3CCl_2F$ | $CCl_2F_2$ | |
| $CH_2ClCH_2F$ | $CH_3ClF_2$ | $CClF_3$ | $CHClFCHCl_2$ |
| $CH_3CHCl_2$ | $CHCl_2CHCl_2$ | $CH_3CH_2F$ | $CHF_2CHCl_2$ |

-continued

| Halocarbon Reactants | | Fluorinated Hydrocarbon Products | |
|---|---|---|---|
| $CH_3CHClF$ | $CHClFCHCl_2$ | $CH_2ClCH_2F$ | $CHF_2CHClF$ |
| $CCl_3CH_2Cl$ | $CHF_2CHCl_2$ | $CH_2FCH_2F$ | $CHF_2CHF_2$ |
| $CCl_2FCH_2Cl$ | $CHF_2CHClF$ | $CH_3CHClF$ | $CF_3CH_2CH_2F$ |
| $C_3CFBrCF_2CF_3$ | | | |
| $CF_3CH_2CH_2Cl$ | $CHClFCCl_3$ | $CClF_2CHCl_2$ | $CF_3CF_2CF_3$ |
| $CF_3CF_2CH_2Cl$ | $CHClFCCl_2F$ | $CF_3CHCl_2$ | $CF_3CF_2CF_2CF_3$ |
| $CF_3CFBrCF_2Br$ | $CHF_2CCl_3$ | $CF_3CHClF$ | $CF_2ClCH_2F$ |
| $CF_3CF_2CFBrCF_2Br$ | | $CHF_2CClF_2$ | $CH_3CF_2Cl$ |
| $CF_3CHCl_2$ | $CHClFCClF_2$ | $CF_3CHF_2$ | $CHClFCH_2F$ |
| $CHF_2CCl_2F$ | $CHF_2CClF_2$ | $CHF_2CH_2Cl$ | $CHF_2CH_2F$ |
| $CH_2CCl_3$ | $CHFClCHFCl$ | $CF_3CF_2CHF_2$ | $CF_3CF_2CHClF$ |
| $CFCl_2CH_2F$ | $CClF_2CH_2F$ | $CF_3CF_2CHCl_2$ | $CF_3CHFCF_3$ |
| $CHCl_2CH_2Cl$ | $CHClFCH_2Cl$ | $CF_3CHFCF_2Cl$ | $CF_3CHFCFCl_2$ |
| $CHCl_2CH_2F$ | $CHF_2CH_2Cl$ | $CF_3CH_2CF_3$ | |
| $CF_2ClCH_2CF_2Cl$ | | | |
| $CHFClCH_2F$ | $CH_3CH_2Cl$ | $CF_3CH_2CF_2Cl$ | |
| $CFCl_2CCl_2CHCl_2$ | | | |
| $CCl_3CCl_2CHCl_2$ | $CF_3CF_2CHCl_2$ | $CF_2ClCCl_2CHCl_2$ | $CF_3CCl_2CHCl_2$ |
| $CFCl_2CCl_2CHCl_2$ | $CF_2ClCCl_2CHCl_2$ | $CF_3CClFCHCl_2$ | |
| $CF_3CCl_2CHCl_2$ | $CF_3CClFCHCl_2$ | | |
| $CF_3CF_2CHFCl$ | $CCl_3CClFCHCl_2$ | | |
| $CCl_3CF_2CHCl_2$ | $CCl_3CF_2CHClF$ | | |
| $CCl_3CF_2CHF_2$ | $CCl_3CCl_2CHFCl$ | | |
| $CCl_3CCl_2CHF_2$ | $CF_3CH_2CF_2Cl$ | | |
| $CF_2ClCH_2CF_2Cl$ | $CFCl_2CH_2CF_2Cl$ | | |
| $CFCl_2CH_2CFCl_2$ | $CCl_3CH_2CFCl_2$ | | |
| $CCl_3CH_2CCl_3$ | | | |

The molten composition is a basically well-known potassium acid fluoride composition. It is readily prepared by reaction of the potassium chloride or fluoride with hydrogen fluoride. When molten, they exist largely as potassium cations, $K^+$, and acid fluoride anions, $[H_nF_{n+1}]^-$, where "n" is a number of at least 0.5, depending on the number of molecules of HF associated with the fluoride ion. It is convenient, however, to represent them as KF.nHF, where "n" is as above. For the purposes of this invention, "n" will normally not be greater than about 2, preferably not greater than about 1.5, more preferably not greater than 1. It will be appreciated that when n=1, the acid fluoride is a hydrogen difluoride, commonly referred to as a "bifluoride"; when n=2, the acid fluoride is a dihydrogen trifluoride; and when n=1.5 the acid fluoride is a mixture of bifluoride and dihydrogen trifluoride. When an additive such as 50 mole % of KF is used along with 50 mole % of the bifluoride, then n=0.5.

In general, the higher the value of "n", the lower the melting point of the potassium acid fluoride, as illustrated in the table below. The table lists melting points of the potassium acid fluorides as a function of "n" (HF content). Variations in the melting point for the same acid fluoride may be attributed to deviations from stoichiometry or trace impurities, e.g. water in the fluorides, etc. or to the determination method employed.

TABLE A

| | Melting Points (°C.) of Potassium Fluorides and Bifluorides | | |
|---|---|---|---|
| Potassium | Fluoride[1] (°C.) | n = 1 Bifluoride (°C.) | n = 2 Dihydrogentrifluoride (°C.) |
| | 880 | 226[2], 238[3] | approx. 72 |

[1]Lange's Handbook of Chemistry - 10th ed., McGraw Hill, 1961.
[2]Chaudhuri et al., Chem. Ind. (London), 88 (1979).
[3]Westrum et al., J. Chem. Thermodynamics 10, 835 (1979).

The potassium acid fluorides may be used alone or in mixtures with one another, also, singly or as mixtures with up to 50 mole percent of another alkali metal acid fluoride or chloride, e.g., lithium, sodium, rubidium or cesium acid fluoride or acid chloride or one or more alkali metal fluorides and/or other alkali metal halides, e.g. chlorides. The bifluorides of K alone or in mixtures, are preferred, because of the low melting point. Lithium, sodium, rubidium and/or cesium fluorides or chlorides, preferably fluorides, may be employed in minor amounts mixed with the potassium bifluorides. Less preferred but useful are minor amounts of the fluorides or chlorides of Ca, Sr, Ba, B, Al or La. Even less preferred but still useful are minor amounts of the fluorides or chlorides of Ti, Zr, Hf, V, Nb, Ta, Cr, Mo, Fe, Co, Ni, Cu, Zn, Ag, Mn, Hg, Cd, Sn, Pb, and Sb.

Molten salt compositions containing up to 50 mole % potassium fluoride along with the bifluoride constitute a preferred aspect of the invention. It is believed that such compositions contain free fluoride ion.

Any of the alkali metal fluorides may be used as the "free" fluoride ion source in mixtures with the K bifluorides provided the bifluoride-fluoride mixtures are molten at the desired fluorinating temperature. The "free" fluoride content is generally in the range of about 0.05 to 1 mole per mole of bifluoride, preferably 0.1 to 0.5. Practically speaking, the existence of "free" fluoride in mixed acid fluoride-fluoride salts depends upon the presence of bifluoride since any higher acid fluoride will consume fluoride.

Specific embodiments of this invention are illustrated in the examples which follow, this Example 5 being the best mode contemplated for performing the invention.

The examples were conducted in a 600 ml autoclave composed of stainless steel, "Inconel" alloy or "Hastelloy". The autoclave was equipped with a gas feed tube, an outlet tube, a stirrer, a heating mantle controlled by a thermocouple centered within the reactor and a pressure transducer for monitoring pressure within the autoclave. The outlet tube was connected is series with a primary gas scrubber containing aqueous caustic, a similarly constituted back-up scrubber, and a gas chromatograph (GC) adapted to automatically sample and analyze gaseous effluent from the reactor. In some examples, the GC results were confirmed with a mass spectrometer (MS). All reactants employed were anhydrous. The gas chromatograph (GC) was a "Hewlett Packard" 5880 model utilizing a flame ionization detector and a customized 4-component column. Analyses of the scrubber solution(s) were carried out using fluoride and chloride specific ion electrodes.

EXAMPLE 1

To a 600 cc stainless steel Parr autoclave was added 350.6 gm (4.49 mole) potassium bifluoride (KHF$_2$); 4.64 gm (1.3 wt.%) R$_f$SO$_3$Li surfactant where R$_f$ is a perfluoroalkyl of C$_{6-8}$ F$_{13-17}$; and 117 gm (0.99 mole) CF$_3$CH$_2$CL (HCFC-133a). The reactor was sealed and heated to 300° C. With vigorous agitation provided by mechanical means. After 40 minutes, the contents were sampled and found to contain 31.8% HCFC-134a.

EXAMPLE 2

To a 600 cc Hastalloy C autoclave was added 303.8 gm (2 mole) CsF, 174.3 gm (3 mole) KF and 80 gm (4 mole) HF. The reactor was fitted with a back pressure regular set at 300 psig and HCFC-133a was fed to the reactor (as a liquid under pressure) by means of a high pressure liquid chromatography pump and at a constant rate of 1.267 gm/minute over a 6 hour run time. Conversion of HCFC-133a was 55% with a selectivity to HFC-134a of 99+% during the first three hours. Conversion of HCFC-133a decreased slowly to 19% over the next three hours, while selectivity to HFC-134a remained ca. 99%.

EXAMPLE 3

To a 600 cc Hastalloy C autoclave was added 303.8 gm (2 mole) CsF, 174.3 gm (3 mole) KF and 80 gm (4 mole) HF. The reactor was fitted with a back pressure regulator set at 300 psig and HCFC-133a was fed to the reactor (as a liquid under pressure) by means of a high pressure liquid chromatography pump and at a constant rate of 1.92 gm/minute over a 2.2 hour run time. Conversion of HCFC-133a was 34% with a selectivity to HFC-134a of 99+% during the first 1.3 hours. Conversion of HCFC-133a decreased slowly to 22% over the next 0.9 hours, while selectivity to HFC-134a remained ca. 99%.

EXAMPLE 4

To a 600 cc Hastalloy C autoclave was added 303.8 gm (2 mole) CsF, 174.3 gm (3 mole) KF and 80 gm (4 mole) HF. The reactor was fitted with a back pressure regulator set at 300 psig and HCFC-133a was fed to the reactor (as a liquid under pressure) by means of a high pressure liquid chromatography pump and at a constant rate of 0.55 gm/minute over a 7 hour run time. Conversion of HCFC-133a was 67% with a selectivity to HFC-134a of 99+% during the first 4 hours. Conversion of HCFC-1133a decreased slowly to 33% over the next three hours, while selectivity to HFC-134a remained ca. 99%.

EXAMPLE 5

To a 600 cc Hastalloy C autoclave was added 303.8 gm (2 mole) CsF, 174.3 gm (3 mole) KF and 80 gm (4 mole) HF. The reactor was fitted with a back pressure regulator set at 450 psig and HCFC-133a was fed to the reactor (as a liquid under pressure) by means of a high pressure liquid chromatography pump and at a constant rate of 1.5 gm/minute over a 3 hour run time. Conversion of HCFC-133a was 58% with a selectivity to HFC-134a of 99+% during the first 1.5 hours. Conversion of HCFC-133a decreased slowly to 38% over the next 1.5 hours, while selectivity to HFC-134a remained ca. 99%.

What is claimed is:

1. A process for the halogen exchange fluorination of a saturated halocarbon having at least one replaceable halogen other than fluorine to a fluorinated hydrocarbon having at least one more fluorine in the molecule than the saturated halocarbon which comprises the following steps: (1) intimately contacting the saturated halocarbon with an anhydrous molten composition containing at least 50 mole % of a compound having the formula KF.nHF wherein KF is potassium fluoride, HF is hydrogen fluoride and "n" is a number from about 0.5 to about 3, at a temperature within the range of about 30° C. up to a temperature below the decomposition temperature of said halocarbon or said fluorinated hydrocarbon, whichever is lower, at a pressure and for a time sufficient to yield at least one reaction product of said fluorinated hydrocarbon having at least one more fluorine in the molecule than said saturated halocarbon and a residual molten composition at least partially depleted in its fluoride content and enriched in its other-than-fluoride halide content; (2) isolating and recovering the fluorinated reaction product from the residual molten composition.

2. A process as in claim 1 wherein "n" is 0.5.

3. A process as in claim 1 wherein said saturated halocarbon is 2-chloro-1,1,1-trifluoroethane, and said fluorinated hydrocarbon is 1,1,1,2-tetrafluoroethane.

4. A process as in claim 1 wherein said saturated halocarbon is 2-chloro-1,1,1-trifluoroethane, chloroform, carbon tetrachloride, 1,1-dichloro-2,2-difluoroethane, 1-fluoro-1,1,2-triclhoroethane, 2,2-dichloro-1,1,1-trifluoroethane, 1,2-dichloroethane or 1,2-dichloro-1-fluoroethane.

5. A process as in claim 1 wherein "n" is a number from about 0.5 to 1.

6. A process as in claim 1 wherein said temperature is about 200° C. to about 350° C.

7. A process as in claim 1 wherein said pressure is about atmospheric pressure (14.7 psi) to about 1500 psi.

8. A process as in claim 1 wherein said contacting step involves a period of 0.5 minute to about 120 minutes.

9. The process of claim 1 wherein said residual molten composition is treated with hydrogen fluoride to obtain an anhydrous molten composition containing a substantial amount of KF.nHF in said molten composition and HX wherein X is the halide that is other than fluoride.

10. A process for the fluorination of 2-chloro-1,1,1-trifluoroethane comprising (1) intimately contacting 2-chloro-1,1,1-trifluoroethane with molten KF.nHF wherein KF is potassium fluoride, HF is hydrogen fluoride and "n" is a number from about 0.5 to 1 at a temperature of about 180° C. to about 350° C. to produce 1,1,1,2-tetrafluoroethane as a gas and cooling said gas to recover liquid 1,1,1,2-tetrafluoroethane.

11. A process as in claim 1 wherein hydrogen fluoride and said halohydrocarbon are cofed continuously to contact said anhydrous molten composition to produce said fluorinated halohydrocarbon and hydrogen chloride while regenerating said molten composition.

* * * * *